United States Patent [19]

Berg et al.

[11] Patent Number: 5,258,454
[45] Date of Patent: Nov. 2, 1993

[54] PEPTIDE SYNTHESIS METHOD AND SOLID SUPPORT FOR USE IN THE METHOD

[75] Inventors: Rolf H. Berg, Frederiksberg; Kristoffer Almdal, Copenhagen; Walther B. Pedersen, Roskilde; Arne Holm, Holte, all of Denmark; James P. Tam, New York, N.Y.; Robert B. Merrifield, Cresskill, N.J.

[73] Assignee: Riso National Laboratory, Roshilde, Denmark

[21] Appl. No.: 882,059

[22] Filed: May 12, 1992

Related U.S. Application Data

[63] Continuation of Ser. No. 398,846, Aug. 25, 1989, abandoned, which is a continuation-in-part of Ser. No. 239,525, Sep. 1, 1988, abandoned.

[51] Int. Cl.$^5$ .................... C08F 283/00; C08G 63/48; C08G 63/91
[52] U.S. Cl. .................. 525/54.11; 530/333; 530/334
[58] Field of Search ............... 525/54.11; 530/333, 530/334

[56] References Cited

U.S. PATENT DOCUMENTS

| | | | |
|---|---|---|---|
| 3,795,664 | 3/1974 | William et al. | 530/334 |
| 3,951,741 | 4/1976 | Pfaender et al. | 435/68.1 |
| 4,631,211 | 12/1986 | Houghten | 428/35 |
| 4,923,901 | 5/1990 | Koester et al. | 521/53 |

FOREIGN PATENT DOCUMENTS

| | | |
|---|---|---|
| 0065069 | 11/1982 | European Pat. Off. |
| 0187391 | 7/1986 | European Pat. Off. |
| 1544668 | 11/1968 | France |
| 1234982 | 6/1971 | United Kingdom |
| 1344706 | 1/1974 | United Kingdom |

OTHER PUBLICATIONS

Effect of Swelling on Radiation-Induced Grafting of Styrene to Polyethylene, Sueo Machi, Ihab Kamel and Joseph Silverman, (1970).
Garnett and Yen American Counsel Society 1980 "Acid Effects In The Radiation Grafting Of Monomers To Polymers, Particularly Polyethylene".
Odian et al Journal of Applied Polymer Science vol. 7, pp. 245-250 (1963) "Accelerative Effects In Radiation-Induced Graft Polymerization".
Odian et al Journal of Polymer Science, vol. XLII Issue 140 (1960) "The Accelerating Effect of Methanol on the Gamma Radiation Induced Graft Copolymerization of Styrene to Polyethylene".
Odian et al Journal of Polymer Science vol. 55, pp. 663-673 (1961) "Radiation-Induced Graft Polymerization: The Trommsdorff Effect of Methanol".

*Primary Examiner*—Nathan M. Nutter
*Attorney, Agent, or Firm*—Wyatt, Gerber, Burke and Badie

[57] ABSTRACT

A method for the solid-phase synthesis of peptides or proteins in high yield and high purity uses a solid-support consisting of a functionalized polystyrene-grafted polymer substrate, the grafted polystyrene chains being substantially non-cross-linked and having a chain molecular weight, not including optional non-reactive substituents, of at least 200,000, preferably in the range of 600,000-1,200,000. Particularly suitable polymer substrates are substrates of a polyolefin such as polyethylene. The method is particularly well-suited to the compartmentalized synthesis of a multitude of peptides or proteins in a parallel and substantially simultaneous fashion.

Preferred embodiments of a solid support for performing the synthesis are prepared from thin polyethylene sheet or film which has been grafted with polystyrene chains in a radical-initiated process in which the polyethylene sheet or film is immersed in a solution of optionally substituted styrene monomer in an alcohol such as methanol, the volume percentage of styrene in the solution preferably being about 30% v/v, and subjected to gamma irradiation.

36 Claims, 4 Drawing Sheets

Boc-Ala-Asp(OBzl)-Lys(2Cl-Z)-Ala-Asp(OBzl)-
    70
Val-Asp(OBzl)-Val-Leu-Thr(Bzl)-Lys(2Cl-Z)-
    76
Ala-Lys(2Cl-Z)-Ser(Bzl)-Gln-OCH$_2$-C$_6$H$_4$-CH$_2$-CO-
              84
NH-CH$_2$-polystyrene-grafted polyethylene sheet

Fig. 1

| | PEPTIDE | SEQUENCE | | | |
|---|---|---|---|---|---|
| | | 7 | 12 | 14 | 21 |
| 1 | MELITTIN-(7-21) | LYS-VAL-LEU-THR-THR-GLY-LEU- | PRO-ALA-LEU-ILE-SER-TRP-ILE-LYS-OH |
| 2 | [D-PRO[14]]MELITTIN-(7-21) | LYS-VAL-LEU-THR-THR-GLY-LEU- | D-PRO-ALA-LEU-ILE-SER-TRP-ILE-LYS-OH |
| 3 | [GLY[14]]MELITTIN-(7-21) | LYS-VAL-LEU-THR-THR-GLY-LEU- | GLY -ALA-LEU-ILE-SER-TRP-ILE-LYS-OH |
| 4 | [LYS[14]]MELITTIN-(7-21) | LYS-VAL-LEU-THR-THR-GLY-LEU- | LYS -ALA-LEU-ILE-SER-TRP-ILE-LYS-OH |
| 5 | [ASP[14]]MELITTIN-(7-21) | LYS-VAL-LEU-THR-THR-GLY-LEU- | ASP -ALA-LEU-ILE-SER-TRP-ILE-LYS-OH |
| 6 | [ASN[14]]MELITTIN-(7-21) | LYS-VAL-LEU-THR-THR-GLY-LEU- | ASN -ALA-LEU-ILE-SER-TRP-ILE-LYS-OH |
| 7 | [SER[14]]MELITTIN-(7-21) | LYS-VAL-LEU-THR-THR-GLY-LEU- | SER -ALA-LEU-ILE-SER-TRP-ILE-LYS-OH |
| 8 | [LEU[14]]MELITTIN-(7-21) | LYS-VAL-LEU-THR-THR-GLY-LEU- | LEU -ALA-LEU-ILE-SER-TRP-ILE-LYS-OH |
| 9 | [PHE[14]]MELITTIN-(7-21) | LYS-VAL-LEU-THR-THR-GLY-LEU- | PHE -ALA-LEU-ILE-SER-TRP-ILE-LYS-OH |
| 10 | [D-PHE[14]]MELITTIN-(7-21) | LYS-VAL-LEU-THR-THR-GLY-LEU- | D-PHE-ALA-LEU-ILE-SER-TRP-ILE-LYS-OH |
| 11 | [VAL[14]]MELITTIN-(7-21) | LYS-VAL-LEU-THR-THR-GLY-LEU- | VAL -ALA-LEU-ILE-SER-TRP-ILE-LYS-OH |
| 12 | [LEU[12], GLN[14]]MELITTIN-(7-21) | LYS-VAL-LEU-THR-THR-LEU-LEU- | GLN -ALA-LEU-ILE-SER-TRP-ILE-LYS-OH |
| 13 | [LEU[12], LYS[14]]MELITTIN-(7-21) | LYS-VAL-LEU-THR-THR-LEU-LEU- | LYS -ALA-LEU-ILE-SER-TRP-ILE-LYS-OH |

Fig. 3

PEPTIDE SYNTHESIS METHOD AND SOLID SUPPORT FOR USE IN THE METHOD

RELATED APPLICATION

This application is a continuation of application Ser. No. 398,846 filed Aug. 25, 1989 now abandoned which is a continuation-in-part of application Ser. No. 239,525 filed Sep. 1, 1988, now abandoned.

FIELD OF THE INVENTION

The present invention concerns a method and a solid support for the solid-phase synthesis of peptides or proteins in high yield and in high purity. The method is well suited both to the synthesis of a single peptide or protein and to the parallel and substantially simultaneous synthesis of a multitude thereof. In particular, the invention concerns a method employing a polymer substrate grafted with polystyrene chains as the solid support, the polystyrene chains optionally further bearing substituents which are not reactive under the conditions prevailing in the synthesis, and having an estimated molecular weight, not including optional substituents, of at least 200,000. The invention employs conventional chemical methodology and is readily adapted to both analytical (microgram) and preparative (milligram or larger) scale synthesis. Furthermore, the invention is adaptable to both batchwise and continuous-flow procedures operating manually, semi-automatically or fully automatically.

BACKGROUND OF THE INVENTION

Present day solid-phase methods for the synthesis of peptides or proteins are largely based on the original methodology developed by Merrifield, employing a functionalized cross-linked styrene/divinyl-benzene copolymer, the cross-linked copolymer having been formed by the polymerization of styrene monomer to which has been added a few percent (typically about 2%) of divinylbenzene. This copolymer is generally provided in the form of beads or particles, often with a dominant particle size of 20–80 $\mu$m. The functionalization originally preferred by Merrifield [see e.g. J. Am. Chem. Soc. 85, 2149 (1963)] was a functionalization of the aromatic rings of the copolymer with chloromethyl groups, introduced via reaction of the solid copolymer with $SnCl_4$/chloromethyl methyl ether, although a number of other functionalities, including aminomethyl, $\alpha$-aminobenzyl and $\alpha$-amino-4-methylbenzyl, have subsequently been employed. Regardless of its nature, the purpose of the functionality is normally to form an anchoring linkage between the copolymer solid support and the C-terminal of the first amino acid which it is desired to couple to the solid support. More recent refinements of the Merrifield methodology have included the further introduction, between a functionality (e.g. one of the above-mentioned functionalities) on the polystyrene chains and the C-terminal of the first amino acid which is to be coupled, of a bifunctional "spacer" or "handle" group whose reactivity is tailored inter alia to meet desired requirements with respect both to the coupling of the first amino acid to the solid support and/or to the ease with which the completed, synthesized peptide or protein chain is cleaved from the solid support. Examples of such spacer groups include the phenylacetamidomethyl (Pam) and the p-alkoxybenzyl ester systems. A recent review dealing with the development of solid-phase peptide synthesis methodology since its introduction by Merrifield is given by Barany et al. [Int. J. Peptide Protein Res. 30, 705–739 (1987)].

Recent advances in biotechnology, particularly in the area of recombinant DNA, have produced a unique situation: the availability and rapid accumulation of many new protein sequences with undefined or unknown function and/or unknown biological activity. Detailed structural analysis by site-directed mutagenesis or similar molecular engineering has provided a useful approach concerning the roles of amino acid residues in active sites of proteins.

However, specific information concerning biologically active functional subunits containing ca. 5–40 amino acid residues is preferably obtained through chemical synthesis. Current solid-phase technology is quite sufficient to yield such peptides reliably and in high purity, but the conventional method of solid-phase peptide synthesis via a "linear" mode of approach produces only one peptide per synthesis.

A method employing a "simultaneous" or "parallel" mode of approach to the synthesis of peptides is thus desirable, thereby facilitating the production of a large number of peptides which can, for example, be used to define and map the functional entities of proteins.

A basic feature of the solid-phase technique of peptide synthesis is that in each elongation of the peptide chain with a further amino acid, all treatment steps are repetitive of the previous cycle with the possible exception of the amino acid coupling step itself, in which a further amino acid that may or may not be identical with that coupled in the preceding cycle is coupled to the peptide chain. Thus, a parallel, substantially simultaneous synthesis of more than one peptide can be achieved by performing in parallel the repetitive steps, such as deprotection, neutralization, and washing, which are common to the parallel syntheses. The major technical difficulty is the attainment of compartmentalization of each amino acid coupling step so that cross-contamination will not occur.

Two different methods have recently been proposed for the substantially simultaneous synthesis of a number of peptides:

The first of these methods [Geysen et al., Proc. Natl. Acad. Sci. USA. 81, 3998–4002 (1984) and 82, 178–82 (1985)]was devised for rapid screening of peptide epitopes via ELISA (Enzyme Linked Immunosorbent Assay) in 96-microtiter wells. It utilizes acrylic acid-grafted polyethylene rod-and-96-microtiter wells to immobilize growing peptide chains and to perform the compartmentalized synthesis. However, while highly effective, the method is not applicable on a preparative scale, i.e. to the preparation of milligram quantities. The second method [Houghten, Proc. Natl. Acad. Sci. USA. 82, 5131–35 (1985)] utilizes a "tea bag" containing the traditionally used polymer beads to compartmentalize the synthesis, portions of peptidylresin beads being kept apart in sealed bags of fine-mesh polypropylene net. The latter method is relevant to the preparation of milligram quantities.

The obvious advantages of a method permitting the parallel and substantially simultaneous synthesis of a multitude of peptides are the attendant saving in time and the redundancy of the repetitive labour involved in accomplishing the synthesis of each peptide individually.

BRIEF DISCLOSURE OF THE INVENTION

The present invention comprises all the favorable aspects of both of the above-mentioned methods and, in addition, offers the advantages, already mentioned, of providing the desired peptide(s) or protein(s) in high yield and high purity, and being equally well adaptable to both analytical and preparative scale syntheses. The invention will greatly benefit studies in structure-activity relationships, investigations such as mapping of antigenic epitopes, determination of details of hormone-receptor interactions and screening for pharmacologically active peptidyl drugs, as well as being of great value in studies concerning the molecular organization of functional subunits of proteins in general.

The invention is based on the provision and use of a solid support comprising a polymer substrate to which are grafted long and substantially non-cross-linked polystyrene chains which, under these conditions and presumably owing to the easy steric access thereto, function as particularly efficient solid-phase carriers for the peptides to be synthesized.

The invention makes use of the insolubility of non-cross-linked polyolefins, e.g. polyethylene, in all organic solvents at ambient temperature. As the grafted polymer is still a thermoplastic material and soluble at elevated temperatures, reshaping is also possible.

BREIF DESCRIPTION OF THE FIGURES

FIG. 1. Protection scheme for the solid-phase assembly of [$Asp^{76}$]hPTH fragment (70–84) on 443 wt % polystyrene-grafted polyethylene.

FIG. 2. Analytical HPLC chromatograms of (A) crude H-Lys-Ala-Lys-Ser-Gln-OH, (B) crude H-Val-Asp-Val-Leu-Thr-Lys-Ala-Lys-Ser-Gln-OH, and (C) crude H-Ala-Asp-Lys-Ala-Asp-Val-Asp-Val-Leu-Thr-Lys-Ala-Lys-Ser-Gln-OH on $\mu$BONDAPAK ™ $C_{18}$ (300×3.9 mm, 10 $\mu$m). Buffer A: $H_2O$/0.095% $CF_3COOH$; buffer B: 90% acetonitrile/10% $H_2O$/0.072% $CF_3COOH$; flow rate 1.3 ml/min.

FIG. 3. The amino acid sequences of melittin-(7–21) and melittin-(7–21) analogs.

FIG. 4. Analytical HPLC chromatograms of crude melittin-(7–21) and analogs after low/high HF-cleavage (before lyophilization). Chromatogram 1 is that for crude melittin-(7–21), i.e. peptide 1, chromatogram 2 is that for crude peptide 2, etc. Buffer A: 5% $CH_3CN$/95% $H_2O$/0.0445% TFA; buffer B: 60% $CH_3CN$/40% $H_2O$/0.0390% TFA; linear gradient: 5–95% of B in 30 min.; flow rate 1.5 ml/min.; column: Vydac $C_{18}$ (0.46×25 cm).

DETAILED DESCRIPTION OF THE INVENTION

Figure 2:
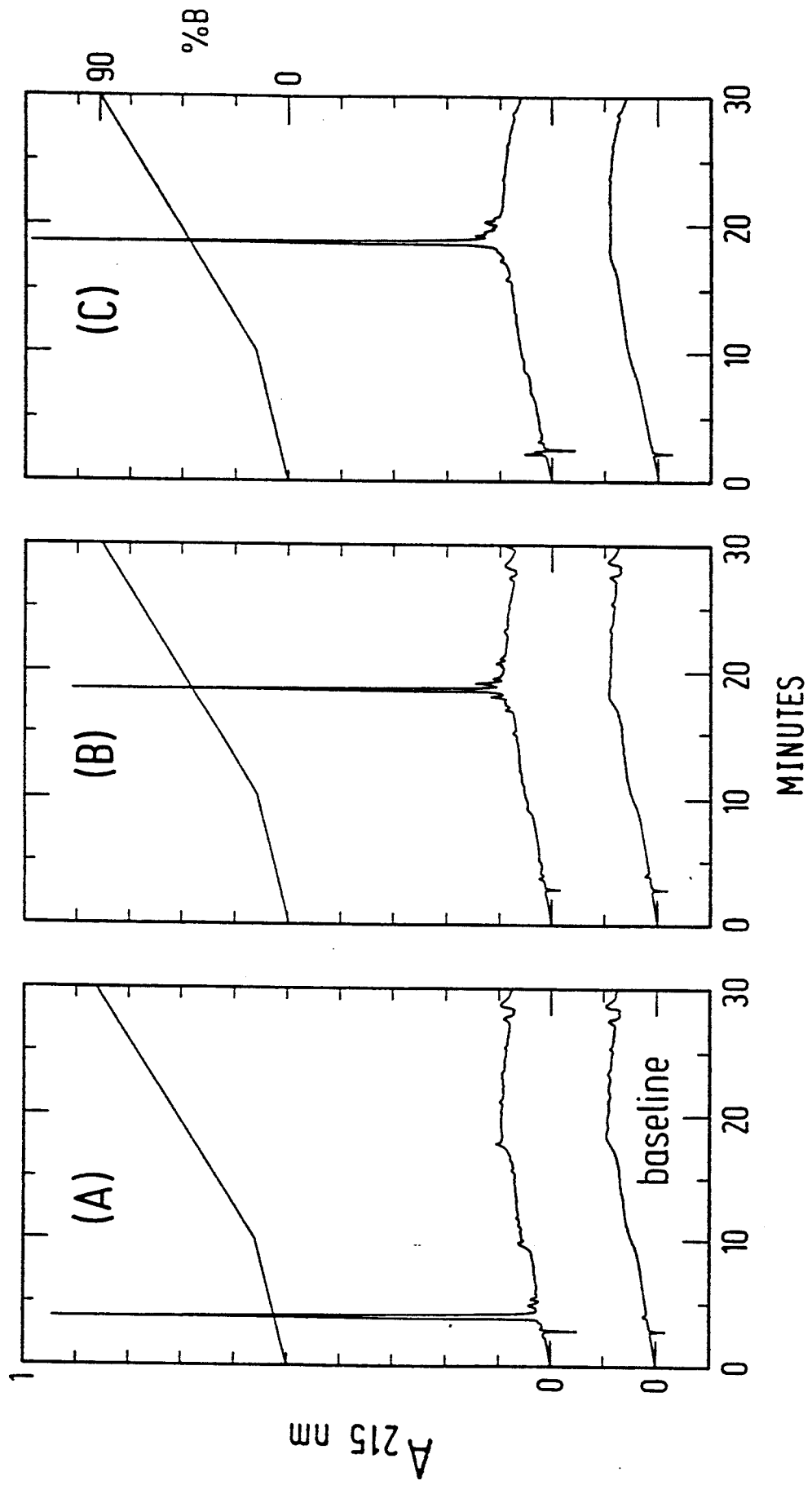

In one aspect of the present invention a method for the synthesis of a peptide or a protein is provided, the method comprising the steps of:

A) providing a polymer substrate grafted with polystyrene chains, said polystyrene chains optionally further bearing substituents which are not reactive under the conditions prevailing in the synthesis, the estimated molecular weight of substantially all of the polystyrene chains grafted to the polymer, not including optional substituents, being at least 200,000, at least part of the polystyrene chains of the polystyrene-grafted polymer substrate being functionalized with a chemical functionality facilitating the formation of an anchoring linkage between the polystyrene moiety and an at least N-protected and optionally carboxyl terminal derivatized amino acid, B) coupling an N-protected and optionally carboxyl terminal derivatized amino acid to the functionalized polystyrene moiety, said functionality and said N-protected and optionally carboxyl terminal derivatized amino acid being adapted to each other such that the anchoring linkage formed can subsequently be cleaved substantially without degradation of the peptide or protein chain which is to be synthesized, C) removing the N-protecting group from an N-protected amino or substituted amino group of the coupled and N-protected amino acid, such that reaction of the amino or substituted amino group of the coupled amino acid with a carboxyl group or an activated carboxyl group of a further amino acid is facilitated, D) reacting said amino or substituted amino group of the last-coupled amino acid with a carboxyl group or an activated carboxyl group of a further N-protected amino acid so as to form a peptide bond between the two amino acid moieties, E) optionally removing the N-protecting group from an N-protected amino or substituted amino group of the last-coupled N-protected amino acid, such that reaction of the amino or substituted amino group of the latter amino acid with a carboxyl group or activated carboxyl group of a further N-protected amino acid is facilitated, F) in those cases where step E) has been performed, repeating steps D) and E) a desired number of times, G) optionally removing some or all protecting groups possibly remaining on the amino acid moieties of the synthesized peptide or protein chain, H) optionally cleaving the linkage anchoring the synthesized peptide or protein chain to the functionalized polystyrene moiety, and I) optionally removing any further undesired group from the synthesized peptide or protein chain, The term polymer substrate as used in the present context denotes any suitable polymer which may be grafted as described and which in itself is substantially insoluble in and inert towards the reaction media used in the synthesis. Suitable polymers may be selected, for example, from polyamides, such as nylon, polyimides, poly(paraxylylenes), poly(halofluoroalkenes), such as poly(tetrafluoroethylene) or poly(chlorotrifluoroethylene), phenol-formaldehyde polymers and polyolefins, such as polypropylene and polyethylene. The polymer substrate may be fashioned in any suitable form, for example a sheet, film, bead, pellet, disc, ring, tube, rod or net. In preferred embodiments of methods for peptide or protein synthesis according to the present invention, the polymer substrate is low-density polyethylene in the form of a sheet or film, although experiments indicate (vide infra) that high-density polyethylene is also suitable.

The polystyrene chains grafted to the polymer substrate may be chains of polystyrene itself or of polystyrene which has been substituted to some extent with substituents which are not capable of reaction under the conditions prevailing in the synthesis. Such substituents may suitably be, for example, alkyl substituents, such as methyl, ethyl, propyl or butyl, alkoxy substituents, such as methoxy, ethoxy, propoxy and butoxy, or aryloxy substituents, such as phenoxy. The substitution will preferably take the form of substitution in the aromatic rings by one or more substituents, e.g. one or more of the above-mentioned substituents, although substitution at non-aromatic carbon atoms of vinyl group origin may also be envisaged. In preferred embodiments of methods for peptide or protein synthesis according to the present invention, the polymer substrate in these cases being polyethylene, the grafted polystyrene chains are chains of non-substituted polystyrene.

It is believed to be particularly advantageous that the polystyrene chains grafted to the polymer substrate are of a molecular weight, not including optional substituents present on the polystyrene chains, of at least 200,000. In a further aspect of the present invention, polystyrene chains fulfilling this condition may suitably be formed by a substantially radical-initiated reaction between the polymer substrate and optionally substituted styrene monomer present in a solution of the monomer in an organic solvent. Experiments have shown (vide infra) that when a polyethylene sheet or film is grafted with polystyrene chains under conditions where the polyethylene sheet or film is immersed in solutions, of varying concentration, or styrene monomer in a solvent such as methanol, the radical-initiated reaction being achieved by 2-radiation, not only does a grafting reaction occur, but non-grafted (i.e. free) polystyrene chains are formed. While there at present is no obvious, straightforward way of determining accurately the molecular weight of the grafted polystyrene chains themselves, the molecular weight of the non-grafted polystyrene chains formed may readily be determined by, e.g., so-called "size-exclusion chromatography". It has been found that when pure styrene monomer is used, i.e. no methanol is present, the molecular weight of the non-grafted polystyrene chains (denoted hereafter as "homopolymer") occluded in the sheet (and extracted from the sheet with dichloromethane) which are formed under a certain set of γ-radiation conditions is predominantly about 180,000, and that the predominant molecular weight of the homopolymer increase with increasing methanol content of the styrene monomer/methanol solution; for example, in 70:30 (v/v) methanol/styrene the predominant molecular weight ($M_{peak}$) is about 1,000,000.

Results obtained with polystyrene-grafted polyethylene sheet grafted to various extents give strong indications that the molecular weight of the homopolymer occluded in the sheet and that of the grafted polystyrene chains correspond quite well, as will be explained at greater length in the following:

Size-exclusion chromatography establishes a relationship between species molecular weight and retention volume, the so-called "calibration curve". The molecular weight of a given fraction of, for example, polystyrene homopolymer with a particular retention volume is determined by comparison with retention volumes for polystyrene standards of known molecular weight. However, since no polystyrene-grafted polyethylene standards of known chain molecular weight are available, the best that can be done is to compare with the retention volumes of polystyrene standards under the same solution conditions.

The grafted sheet, the homopolymer and the polystyrene standards may be dissolved, e.g., in hot xylene, and in several such experiments the molecular weight of the most abundant fraction ($M_{peak}$) of homopolymer was found to be ca. 1,000,000. The $M_{peak}$ value found for the polystyrene-grafted polyethylene sheet on the basis of the above-mentioned comparison with retention volumes of polystyrene standards was ca. 3,000,000 and upwards [it can be envisaged that a certain proportion of the individual polyethylene chains may be grafted with more than one polystyrene moiety, and the $M_{peak}$ value determined in the above manner for the polystyrene-grafted polyethylene may consequently be similar to or higher than that for the corresponding occluded polystyrene homopolymer].

Further evidence for the validity of the above-described molecular weight estimation procedure can also be derived from the above-mentioned experiments as follows:

The abundance, $n_i$, of a particular fraction, i, of molecular weight $M_i$ is proportional to the height of the distribution curve at the retention volume corresponding to $M_i$. The so-called "weight average molecular weight", $M_w$, is then given by:

$$M_w = \Sigma n_i \times M_i^2 / \Sigma n_i \times M_i,$$

while the so-called "number average molecular weight", $M_n$, is given by:

$$M_n = \Sigma n_i \times M_i / \Sigma n_i$$

Current theory concerning radical-initiated polymerisation predicts a $M_w/M_n$ ratio (the "polydispersity") of 2.0. A value of ca. 2 was found for the homopolymer, and the value found for the polystyrene-grafted polyethylene was also ca. 2, which may be taken as an indication that the polystyrene chains grafted to the polyethylene substrate have grown in essentially the same manner as the homopolymer, thereby lending further credence to the molecular weight estimation procedure outlined above. The estimated molecular weights referred to in the present description and claims were estimated in the above-described manner.

It is thus believed that the molecular weight of occluded homopolymer formed under a given set of conditions (solvent, styrene concentration, temperature, γ-radiation intensity and duration of γ-irradiation) closely reflects the molecular weight of the grafted polystyrene chains formed under the same set of conditions, the molecular weight determined for the homopolymer thus being taken as an estimate of the molecular weight of the grafted polystyrene chains.

It is also believed that the density of grafting sites on the surface of a polymer substrate, i.e. the number of points of attachment of polystyrene chains per unit surface area, as well as the extent of cross-linking of the grafted polystyrene chains, is strongly influenced by the conditions under which grafting takes place, in particular by the nature of an organic solvent used in the grafting process. Hydroxylic organic solvents, particularly alcohols such as methanol, are relatively hydrophilic and are therefore anticipated to be among the poorer solvents which may be chosen to dissolve a relatively hydrophobic substance such as styrene monomer. Thus, the degree of solvation of the monomer by such a solvent is expected to be relatively low by comparison with the degree of solvation which would be expected with a more hydrophobic organic solvent, for example a halogenated aliphatic hydrocarbon such as dichloromethane (dichloromethane being a preferred reaction solvent in solid-phase peptide synthesis methodology, both in general and in the context of the present invention). It is believed that poor swelling or solvation of the grafted polystyrene chains during the grafting process in a solvent such as methanol maintains the mobility of the growing polystyrene chains at a low level thereby leading to retardation of the diffusion-controlled chaintermination processes and thus facilitating the growth of particularly long polystyrene chains.

An attractive feature of the high molecular weight of the grafted polystyrene chains in the context of the present invention is that when functionalized, they may be presumed to behave, with regard to their reactivity towards dissolved reagents, to a large extent as though they were non-grafted (i.e. free) functionalized polystyrene chains in homogeneous solution; the ease with which functionalized, grafted polystyrene chains formed in accordance with the present invention can react with dissolved reagents, including protected and optionally derivatized amino acids, may therefore be regarded as optimal. The apparent substantial absence of cross-linking between the polystyrene chains grafted to the polyolefin facilitates extensive swelling or solvation of the chains by a chlorohydrocarbon solvent (in a preferred embodiment of the present invention dichloromethane) such as generally preferred in solid-phase peptide syntheses. As mentioned previously, in conventional solid-phase peptide synthesis procedures employing "Merrifield-type" methodology, the solid support used is normally a functionalized cross-linked styrene/divinylbenzene copolymer, the cross-linked copolymer having been formed by the polymerization of styrene monomer to which has been added a few percent (typically ca. 2%) of divinylbenzene. This cross-linking reduces the degree of swelling or solvation of the functionalized copolymer matrix relative to that prevailing for functionalized, grafted polystyrene chains formed in accordance with the present invention, and thereby correspondingly reduces the reactivity of the former matrix.

According to the invention, it is preferred that the estimated molecular weight of substantially all of the polystyrene chains grafted to the polymer, not including optional substituents, is in the range of 300,000–1,600,000, in particular 400,000–1,400,000, preferably 600,000–1,200,000. The presently preferred estimated molecular weight of substantially all of the polystyrene chains is 700,000–1,000,000. It is believed that the higher estimated molecular weights of 400,000 and above are particularly advantageous, but on the other hand, the grafting of polystyrene chains of the very highest estimated molecular weights of about 1,000,000 and above appears to have a detrimental effect on the mechanical properties of the polymer substrate, in particular when the substrate is, as is often preferred, in the form of a sheet or film.

The degree of polystyrene chain grafting of the polymer substrate, that is, the weight percentage of polystyrene relative to the polymer substrate, depends, of course, on the length of the polystyrene chains, the grafting site density and the dimensions of the polymer substrate, and may vary within wide limits. Thus, in the case of, e.g., a sheet or film of polymer substrate of thickness in the range of 25 to 100 $\mu$m, the degree of polystyrene chain grafting may be, e.g., from about 5 to about 800% by weight, such as from about 10% to about 700%. Both very low and very high degrees of polystyrene chain grafting, as well as intermediate degrees of grafting, are of value in the context of preferred embodiments of the present invention.

Thus, for analytical purposes, where it is normally desired to be able to synthesize peptide sequences of proteins on a small scale, typically microgram scale, the provision, for example, of a polymer substrate with a relatively low degree of polystyrene chain grafting, such as, e.g. 5 to 200%, normally 10 to 60% (for a sheet or film of polymer substrate of thickness in the range of 25 to 100 $\mu$m), and preferably with a controlled, often low extent of functionalization ensures controlled limitation of the amount(s) of peptide(s) formed.

Polystyrene-grafted polyethylene sheet or film produced as preferred within the context of the present invention is particularly advantageous with respect to analytical aspects of peptide chemistry or biochemistry in that its high degree of transparency to light, particularly visible light, facilitates the use of spectrophotometric techniques, e.g. for the monitoring (for example by an ELISA technique) of antigen/antibody reactions which can be monitored by a subsequent colour reaction and in which the antigen may be a particular peptide sequence synthesized on and remaining anchored to the solid support.

For preparative purposes, where the attainment of the highest possible yield of a peptide or protein is clearly desirable, it is advantageous to use the highest practicable degree of grafting. From an overall point of view, the practical upper limit of the degree of grafting for a sheet or film of polymer substrate of thickness in the range of 25 to 100 $\mu$m (as employed according to preferred embodiments) will often be about 500–600% by weight, although special applications may make it desirable to exceed this range, such as to a degree of grafting of about 700%. On the other hand, the lowest degrees of grafting practicable will normally not be below about 40% for such a thin sheet or film. For most practical purposes, the degree of grafting of such a thin sheet or film will be in the range of about 100–600% and will often be in the range of 200–600% and, for preparative purposes, often preferably 200–400% by weight, which seems to be a suitable range both from the point of view of the yield and efficiency of peptide syntheses performed using functionalized, grafted sheet and from the point of view of mechanical strength of the grafted sheet or film.

As will be apparent from the examples illustrating the invention, extraordinarily high yields of highly pure peptides are obtainable, for example, using preferred embodiments of methods according to the present invention which employ functionalized polystyrene-grafted polyethylene sheet or film formed from a polyethylene substrate in the form of a thin sheet or film of thickness in the vicinity of 50 $\mu$m and with a degree of grafting in the vicinity of 400–500%.

As mentioned above, in one aspect of the invention, the polystyrene-grafted polymer substrate is formed by a substantially radical-initiated reaction between the polymer substrate and optionally substituted styrene monomer present in a solution of said monomer in an organic solvent. As also mentioned above, it is advantageous, from the point of view of obtaining long, substantially non-cross-linked polystyrene chains, to perform the grafting in a solvent in which the growing polystyrene chains are poorly swelled or solvated, such as a hydroxylic organic solvent, in particular an alcohol. Preferred alcohols for this purpose are $C_{1-4}$ aliphatic alcohols. In practice, methanol has been found to be a most suitable solvent, but it is contemplated that also, e.g., ethanol, propyl and isopropyl alcohols, and n-butyl, iso-butyl, sec-butyl and tert-butyl alcohols will be applicable.

The volume percentage (% v/v) of optionally substituted styrene in the solution used for the grafting, such as a solution in a solvent which swells or solvates the growing polystyrene chains poorly, e.g. a hydroxylic solvent as explained above, in particular an alcohol as explained above, such as, e.g., methanol, has a marked influence on the molecular weight of the grafted polystyrene chains formed, in that, at least up to a certain point, the chain-length-increasing effect of the solvent is greater, the greater the volume percentage of the solvent in the solution. Thus, while the volume percentage of optionally substituted styrene in the solution may be within a very broad range, such as between 1 and 95%, this volume percentage will normally be in the range of 10 to 90%, more usually 20 to 80%. A very interesting range for the volume percentage of the optionally substituted styrene in the solution is between 25 and 50%, and as will appear from the examples, a range of 25 to 35%, in other words about 30% by volume, has been found in practice to give supports with excellent properties. An indication of the relation between the volume percentage of styrene in methanol during the grafting process and the resulting estimated polystyrene chain lengths appears from the below-mentioned experiments on the relationship between the volume percentage of the optionally substituted styrene in methanol and the molecular weight of the generated homopolymer at a constant $\gamma$-radiation dose and dose-rate.

The grafting process is very suitably performed by $\gamma$-irradiation in the absence of oxygen and at substantially ambient temperature or slightly elevated temperature, the pressure being equal to the total vapour pressure of the liquid components, optionally supplemented by a moderate pressure of an inert gas such as argon, the total pressure then amounting to about 1 atmosphere. A suitable way to remove oxygen from the reaction system is to subject the system to repeated freezethaw cycles on a high cacuum apparatus. The $\gamma$-irradiation is suitably performed at a dose rate in the range of from about 1 to about 100,000 Gy/hour, in particular about 200-5000 Gy/hour, such as about 300-1000 Gy/hour. It is believed that the intensity of the irradiation is of considerable importance to the obtainment of the desirable configuration with long, substantially non-cross-linked polystyrene chains; if the intensity is too high, the free radical formation will be so high that the grafting will tend to involve a greater number of shorter chains and perhaps a higher degree of cross-linking, both of which are normally not desired.

On the whole, the optimization of chain length, grafting, and optical properties of the support (which is particularly important when the support is a sheet or film) is performed via the choice of polymer, optionally substituted styrene monomer, reaction mixture, radiation dose-rate, and temperature during irradiation.

While the above-described method involving $\gamma$-irradiation is the presently preferred method, it is contemplated that polystyrene-grafted films may suitably be prepared using a different strategy involving conventional radical initiators, such as peroxides, for example hydrogen peroxide, benzoyl peroxide or diacetyl peroxide, or azo compounds as the radical-forming principles. Other radical-forming principles which may be employed are, e.g., ozone and UV-radiation; another particularly interesting radical-forming principle is an electron beam. The important thing is that the method used for the radical generation be one which is suitable for relatively well-controlled radical-initiated growth of the polystyrene chains. It is believed that the conditions mentioned above concerning the importance of the properties of the solvent used also apply in connection with these free radical initiation principles.

It is also contemplated that it may be possible to produce polystyrene/polyethylene block copolymers useful for the present invention in a manner which does not make use of radical initiation. Thus, for example, it is possible using anionic polymerization to synthesize a block copolymer of butadiene and styrene, in which the chain length of the two blocks can be precisely controlled. It is possible to hydrogenate this polymer in such a manner that the polybutadiene block is converted into polyethlene. The polyethylene formed will have such a regular structure that is, in the solid state, will form high-density polyethylene. It is critical to this method that the polyethylene part of the copolymer should form a coherent film. It is contemplated that this can be obtained in the following manner: the ethylene/styrene block copolymer is dissolved in a solvent in which the polystyrene part is soluble at room temperature and higher temperatures but in which the polyethylene part is only soluble when the solvent is hot. An example of such a solvent is xylene. The polymer solution is placed in a mould and slowly cooled to below the temperature at which polyethylene precipitates. When the polyethylene film has been formed, the rest of the solvent is removed.

It is further contemplated that the latter-outlined alternative method of preparation may be extended to the preparation of other polystyrene/polyolefin block copolymers, for example polystyrene/polypropylene block copolymer, by employing diene monomers other than butadiene, e.g. 2-methyl-1,3-pentadiene in the case of polystyrene/polypropylene block copolymer.

While the polystyrene-grafted polymer substrate may be in any suitable form, such as explained above, very interesting embodiments of the invention are such in which it takes the form of a sheet or film. The thickness of the polymer substrate itself, for example a polyethylene substrate, which is the starting material for such a sheet or film, may vary within a wide range and will normally be from 10 tó 10,000 $\mu$m, for most purposes preferably in the range 25 to 1000 $\mu$m, and typically in the range 25 to 100 $\mu$m such as 25 to 75 $\mu$m. The grafting process leads, of course, to an increase in the thickness. Thus, the thinner a sheet or film, the greater will the percentage increase in thickness be for a given set of grafting conditions. As an example, a thin grafted sheet or film may have. a thickness in the range of 25 to 200 $\mu$m.

As the grafted polymer in the form of a sheet or film is a thermoplastic material and soluble at elevated temperatures, reshaping after the grafting process is complete is contemplated as a possibility. Thus, in the case of a polystyrene-grafted polyethylene sheet or film, as preferred in the context of the present invention, it is possible to dissolve the sheet or film in a suitable solvent and allow the solution to cool and the solvent to evaporate to obtain a new "casting" of the polymer support, e.g. as a thinner sheet or film, with the grafted polystyrene chains. The suitable solvent is one which, at a suitably high temperature, dissolves the polymer support with its grafted polystyrene chains (but with retention of the grafting) and which on cooling to a lower temperature is no longer capable of retaining the polymer substrate in solution, but still effectively swells or solvates the polystyrene chains. An example of such a solvent, useful, e.g., for polystyrene-grafted polyethylene, is a xylene or a mixture of xylenes. .

A sheet or film has a number of advantages in the practical performance of peptide or protein synthesis. Thus, e.g., sheet or film may easily be cut out in suitable sizes for arranging in the reaction vessels used, such as any type of known solid-phase peptide synthesis reaction vessels, including flasks, beakers, microbeakers, funnels, wells, columns or nets.

The film or sheet support makes it possible to device new practical ways of handling the peptide synthesis. Thus, e.g., a number of sheet or film pieces may be arranged on a common support and thus be kept together during the various stages of peptide synthesis, e.g. by being exposed together to the various reagents and washing solvents, or the pieces may be arranged in sets, each set being subjected to a particular combination of reaction media.

This latter possibility facilitates efficient "compartmentalization" whereby two or more peptides can be prepared in a parallel and substantially simultaneous manner.

Thus, in one aspect the invention provides a particularly practical method for "compartmentalized" synthesis of peptides and proteins, this aspect being based on the use of a polystyrene-grafted sheet or film as the solid-phase peptide synthesis support. This aspect of the invention may be expressed as a method for the synthesis of one or more peptides or proteins, which method, when two or more peptides or proteins are to be synthesized, permits the parallel and substantially simultaneous synthesis of the desired number of peptides and proteins, the method comprising:

a) providing a plurality of substantially identical polymer substrates grafted with polystyrene chains, said polystyrene chains optionally further bearing substituents which are not reactive under the conditions prevailing in the synthesis, at least part of the polystyrene chains of each polystyrene-grafted polymer substrate being functionalized with a chemical functionality facilitating the formation of an anchoring linkage between the polystyrene moieties and an at least N-protected and optionally carboxyl terminal derivatized amino acid, by optionally physically segregating the members of said plurality of polystyrene-grafted polymer substrates into two or more sets each comprising one or more members of said plurality, coupling an N-protected and optionally carboxyl terminal derivatized amino acid to the functionalized polystyrene moieties of each member of said plurality or, where applicable, each member of each set, the N-protected and optionally carboxyl terminal derivatized amino acid employed being identical for all the members of the plurality or, where applicable, all the members of one set, and, where applicable, further being in accordance with one of the following alternatives;

(i) identical for all the sets,
(ii) when the number of said sets is greater than two, identical for at least two of the sets,
(iii) different for each set, said functionality and said N-protected and optionally carboxyl terminal derivatized amino acid being adapted to each other such that the anchoring linkage formed can subsequently be cleaved substantially without degradation of the peptide or protein chain which is to be synthesized, C) treating each member of said plurality or, where applicable, each member of each said set so as to remove the N-protecting group from an N-protected amino or substituted amino group of the coupled and N-protected amino acid, such that reaction of the amino or substituted amino group of the coupled amino acid with a carboxyl group or an activated carboxyl group of a further N-protected amino acid is facilitated, D) reacting said amino or substituted amino group of the amino acid last coupled to the functionalized polystyrene moieties of each member of said plurality or, where applicable, of each member of each set with a carboxyl group or an activated carboxyl group of a further N-protected amino acid, so as to form a peptide bond between said amino or substituted amino group and said carboxyl group or activated carboxyl group, said further N-protected amino acid being identical for all the members of the plurality or, where applicable, all the members of one set, and, where applicable, further being in accordance with one of the three alternatives mentioned above in connection with step B), E) optionally treating each member of siad plurality or, where applicable, each member of each said set so as to remove the N-protecting group from an N-protected amino or substituted amino group of the last-coupled N-protected amino acid, such that reaction of the amino or substituted amino group of the latter amino acid with a carboxyl group or activated carboxyl group of a further N-protected amino acid is facilitated, F) in those cases where step E) has been performed, repeating steps D) and E) a desired number of times, G) optionally treating each member of said plurality or, where applicable, each member of each said set so as to remove some or all protecting groups possibly remaining on the amino acid moieties of the synthesized peptide or protein chain, H) optionally treating each member of said plurality or, where applicable, each member of each said set so as to cleave the linkage anchoring the synthesized peptide or protein chain to the functionalized polystyrene moieties of each member of said plurality or, where applicable, of each member of each said set, and I) optionally removing any further undesired group from a synthesized peptide or protein chain.

One practical way of handling the polymer support in the form of a sheet or film for compartmentalization purposes is to cut the sheet or film into a desired number of pieces which are then marked indelibly, e.g. by means of graphite-based ink melted into the surface of some part of the sheet or film. Another possibility is to have the various pieces present on one and the same large piece of sheet or film and then treat the different areas (which are suitably marked as described above) jointly or separately as the case may be. Evidently, one embodiment is to allow the pieces to remain on one and the same film as long as the treatments to be performed are the same, and then divide the film into sub-units when the steps to be performed are different.

The chemical functionality facilitating the formation of an anchoring linkage between an at least N-protected and optionally derivatized amino acid and the functionalized polystyrene moiety is suitably a member of, or is derived from a member of the group comprising:

chloro-, bromo- and iodo-substituted alkyl,
amino-substituted alkyl,
amino- and aryl-substituted alkyl,
amino- and alkylaryl-substituted alkyl,
hydroxy-substituted alkyl, the functionality, if derived from any of said group, being a functionality with a spacer group such that a synthesized peptide or protein chain will be cleavable from the polystyrene moiety substantially without degradation of said chain.

According to suitable embodiments of the invention, chloro-substituted alkyl is chloromethyl, amino-substituted alkyl is aminomethyl, amino- and alkyl-substituted aryl is α-aminobenzyl (benzhydrylamino), amino- and alkylaryl-substituted alkyl is selected from the group consisting of α-amino-2-, α-amino-3- and α-amino-4-methylbenzyl (the latter also being known as 4-methylbenzhydrylamino), and hydroxy-substituted alkyl is hydroxymethyl.

Concerning the initial functionalization of the polystyrene-grafted polymer substrate, more than fifty methods have been described in connection with traditional solid-phase peptide synthesis (see Barany and Merrifield in *The peptides*, Vol. 2, Academic Press, N.Y., 1979, pp. 1–284, and Stewart and Young, *Solid Phase Peptide Synthesis*, 2nd Ed., Pierce Chemical Company Ill., 1984), of which reactions for the introduction of chloromethyl (via a chaloromentyl methyl ether/SnCl$_4$ reaction, aminomethyl (via a N-hydroxymethylphthalimide reaction; see Mitchell et al., *Tetrahedron Lett.*, 3795, (1976)) and benzhydrylamino (Pietta and Marshall, *J. Chem. Soc.*, 650 (1970)) groups are the most widely applied. Other reactive functionalities which have been initially introduced include 4-methylbenzhydrylamino and 4-methoxybenzhydrylamino. All of these established methods are in principle useful within the context of the present invention. Preferred embodiments of peptide or protein synthesis methods within the context of the present invention employ aminomethyl as the initial functionality, in that aminomethyl is particularly advantageous with respect to the incorporation of "spacer" or "handle" groups owing to the reactivity of the amino group of the aminomethyl functionality with respect to the essentially quantitative formation of amide bonds to a carboxylic acid group at one end of the spacer-forming reagent. A vast number of relevant spacer- or handle-forming bifunctional reagents have been described (see Barany et al., *Int. J. Peptide Protein Res.*, 30, 705–739 (1987), especially reagents which are reactive towards amino groups, such as the amino group in the aminomethyl function, including a 4-(haloalkyl)aryl-lower alkanoic acid such as 4-(bromomethyl)phenylacetic acid, a Boc-aminoacyl-4-(oxymethyl)aryl-lower alkanoic acid such as Boc-aminoacyl-4-(oxymethyl)phenylacetic acid, N-Boc-p-acylbenzhydrylamine such as N-Boc-p-glutaroylbenzhydrylamine N-Boc-4'-lower alkyl-p-acylbenzhydrylamine such as N-Boc-4'-methyl-p-glutaroylbenzhydrylamine, N-Boc-4'-lower alkoxy-p-acylbenzhydrylamine such as N-Boc-4'-methoxy-p-glutaroylbenzhydrylamine and 4-hydroxymethylphenoxy-lower alkanoic acid such as 4-hydroxymethylphenoxyacetic acid.

Certain functionalities, such as benzhydrylamino, 4-methylbenzhydrylamino and 4-methoxybenzhydrylamino which may be incorporated for the purpose of cleavage of a synthesized peptide or protein chain from the solid support such that the C-terminal of the peptide or protein chain is in amide form, require no introduction of a spacer group, and any such functionality may advantageously be employed in the context of the present invention.

An alternative strategy concerning the introduction of spacer or handle groups is the so-called "pre-formed handle" strategy (see Tam et al., *Synthesis*, 955–57, (1979)), which offers complete control over coupling of the first amino acid, and excludes the possibility of complications arising from the presence of undesired functional groups not related to the peptide or protein synthesis. In this strategy, spacer or handle groups, in general spacer or handle groups of the same types as described above, are reacted with the first amino acid which it is desired to anchor to the solid support, the amino acid being N-protected and optionally protected at other side-chains which are not relevant with respect to the building-up of the desired peptide or protein chain. Suitable N-protecting groups are Boc, normally in combination with benzyl groups for the protection of side chains, and Fmoc, normally in combination with t-butyl for the protection of any side chains (Boc=t-butyloxycarbonyl; Fmoc=9-fluorenylmethyloxycarbonyl), although a number of other possibilities exist which are well known in conventional solid-phase peptide synthesis.

Thus, in those cases in which a spacer or handle group is desirable, the first amino acid to be coupled to the solid support can either be coupled to the free reactive end of a spacer group which has been bound to the initially introduced functionality, for example aminomethyl, or can be reacted with the spacer-forming reagent, which in turn is then reacted with the initially introduced functionality.

Following completion of the coupling of the first amino acid which is to be coupled, the next stage of the solid-phase synthesis is the systematic elaboration of the desired peptide or protein chain. This elaboration involves repeated deprotection/coupling cycles. The temporary protecting group, such as a Boc or Fmoc group as described above, on the last-coupled amino acid is quantitatively removed by a suitable treatment, for example by acidolysis, such as with trifluoroacetic acid, in the case of Boc, or by base treatment, such as with piperidine, in the case of Fmoc, so as to liberate the N-terminal amine function of the last-coupled amino acid.

The next desired N-protected amino acid is then coupled to the N-terminal of the last-coupled amino acid. This coupling of the C-terminal of an amino acid with the N-terminal of the last-coupled amino acid can be achieved in several ways, for example by providing the incoming amino acid in a form with the carboxyl group activated by any one of several methods, including the initial formation of an active ester derivative, or the initial formation of an anhydride. Alternatively, the carboxyl group of the incoming amino acid may be reacted directly with the N-terminal of the last-coupled amino acid with the assistance of a condensation reagent, for example dicyclohexylcarbodiimide or derivatives thereof.

Following the completed assembly of the desired peptide or protein chain, including protecting groups, the next step will normally be deprotection of the amino acid moieties of the peptide or protein chain and cleavage of the synthesized peptide or protein from the solid support. These processes can take place substantially simultaneously, thereby providing the free peptide in the desired form. Alternatively, in cases in which condensation of two separately synthesized peptide or protein chains is to be carried out, it is possible by choosing a suitable spacer group at the start of the synthesis to cleave the desired peptide or protein chains from their respective solid supports, both peptide or protein chains still incorporating their side-chain protecting groups, and finally removing the side-chain protecting groups after, for example, coupling the two side-chain protected peptide or protein chains to form a longer peptide or protein chain. A third possibility, which is particularly relevant for example in the case of analytical aspects of peptide chemistry or biochemistry, is to remove the side-chain protecting groups from the synthesized peptide or protein chain without cleaving the anchoring linkage holding the chain to the solid support.

It is envisaged that polystyrene-grafted polyethylene substrates analogous to those of the present invention, but comprising linker or spacer groups adapted to the particular chemistry in question, may be valuable in the synthesis of single or multiple biopolymer molecules other than peptides. One example would be the synthesis of oligonucleotides, these being conceptually simple to synthesize since only four different reaction compartments are normally required, one for each of the four nucleotide units involved (i.e. A, T, G and C for DNA fragments, or A, G, C and U for RNA fragments). Such syntheses could be carried out in a parallel and substantially simultaneous fashion, in a manner analogous to that described within the context of the present invention.

The following examples illustrate the invention, the abbreviations used being as follows:

LIST OF ABBREVIATIONS

Boc: tert-butyloxycarbonyl
CIZ: 2-chlorobenzyloxycarbonyl
DCC: N,N'-dicyclohexylcarbodiimide
DCU: N,N'-dicyclohexylurea
DIEA: N,N-diisopropylethylamine
DMF: N,N-dimethylformamide
FABMS: Fast atom bombardment mass spectrometry
HOBt: 1-hydroxybenzotriazole
HPLC: high performance liquid chromatography
Pam: phenylacetamidomethyl
PE: polyethylene
PP: polypropylene
SEC: size-exclusion chromatography
SPPS: solid phase peptide synthesis
TFA: trifluoroacetic acid
TFMSA: trifluoromethanesulfonic acid
THF: tetrahydrofuran The abbreviations used for the various amino acids are in accordance with the recommendations of the IUPAC-IUB Comission of Biochemical Nomenclature [J. Biol. Chem., 247, 977–983 (1972)], and refer in all cases to L-configuration amino acids.

EXAMPLE 1

General Procedure for Preparation of Polystyrene-Grafted Polyethylene Sheets

Styrene (99% Aldrich) was passed through basic alumina; in some cases it was further distilled from sodium or from calcium hydride. 20 ml of a 30% (v/v) solution of purified styrene in methanol was placed in an ampoule together with a rectangular strip of low-density PE sheet which had been washed in n-hexane. The sheet used had a thickness of 54 μm. The solution was thoroughly degassed by repeated freeze-thaw cycles on a high vacuum line and the ampoule was then sealed under vacuum. The ampoule and contents were then irradiated in a cobalt gamma-irradiation facility. The irradiation was carried out in two stages, the ampoule being moved from one location in the irradiation source to another between the two stages to ensure as homogeneous a dose distribution as possible. The dose rate was approximately 400 Gy/hour. The highest dose rate used was 417 Gy/hour and the lowest 339 Gy/hour. After irradiation the sheet was extracted in a Soxhlet apparatus with dichloromethane and dried. Specific data are listed in Table 1. It is noteworthy that although there is a clear correlation between the irradiation dose and the extent of the grafting, there is much scatter in the data. This is partly due to the so-called "after effect", the polymerization process continuing to some extent after the irradiation is stopped. As an example of this effect the ampoule containing the sheet irradiated with a total dose of 3.4 kGy to yield a 450% grafted sheet was left outside the irradiation source for 10 hours between the two stages of irradiation. Furthermore, the ampoule was first opened 10 days after completion of irradiation. A similar procedure was used for the sheet irradiated with a total dose of 2.0 kGy to yield 230% grafting.

TABLE 1

| Grafting of PE sheets in methanol/styrene (70% v/v) | | | |
|---|---|---|---|
| Mass of PE sheet (g) | Irradiation dose (kGy) (Irradiation time in hours) | Graft %* | Duration of extraction with CH$_2$Cl$_2$ (hours) |
| 0.2288 | 5.6 (14.0) | 547 | 30 |
| 0.290 | 4.0 (10.0) | 443 | 96 |
| 0.3322 | 3.4 (9.0) | 450 | 330 |
| 0.2742 | 3.0 (8.1) | 220 | 240 |
| 0.3866 | 2.9 (8.0) | 285 | 170 |
| 0.3400 | 2.7 (6.7) | 231 | 90 |
| 0.2398 | 2.4 (6.0) | 173 | 120 |
| 0.3399 | 2.0 (6.0) | 230 | 185 |
| 0.3502 | 1.7 (4.8) | 200 | 182 |
| 0.3710 | 1.7 (5.0) | 180 | 260 |
| 0.3456 | 1.0 (3.0) | 75 | 56 |
| 0.3385 | 1.0 (3.0) | 55 | 114§ |
| 0.3831 | 0.98 (2.8) | 80 | 119 |

*Graft % = [(mass of final sheet) − (mass of polyethylene)] × 100/(mass of polyethylene)
§: The top of the sheet was damaged during the closure of the ampoule.

Sheets with graft % 46, 129 and 331, respectively, have also been prepared.

EXAMPLE 2

Procedure for Grafting on Non-Woven Felt Made from Fibers Consisting of a Polypropylene Core and Another Layer of High-Density Polyethylene The non-woven PP/PE felt was washed with n-hexane and irradiated in a closed ampoule containing a degassed 30% (v/v) solution of purified styrene in methanol in a manner completely analogous to the general procedure described in Example 1. The results are given in Table 2.

TABLE 2

| Grafting of PP/PE non-woven felt in methanol/styrene (70:30 v/v) | | | |
|---|---|---|---|
| Mass of PP/PE felt (g) | Irradiation dose (kGy) (Irradiation time in hours) | Graft %* | Duration of extraction with CH$_2$Cl$_2$ (hours) |
| 0.2400 | 1.6 (4.5) | 86 | 124 |
| 0.2084 | 2.1 (6.0) | 106 | 72 |

*Graft % = [(mass of final sheet) − (mass of polyethylene)] × 100/(mass of polyethylene)

EXAMPLE 3

Influence of Methanol/Styrene Ratio on Grafted Polystyrene Chain Length

The following results were obtained for irradiation of low-density polyethylene sheets in different methanol/styrene mixtures (5 kGy dose, 400 Gy/hour dose rate, room temperature):

| % Methanol in solvent (v/v) | Peak molecular weight of homopolymer |
| --- | --- |
| 0 | 180,000 |
| 20 | 300,000 |
| 40 | 500,000 |
| 70 | 800,000 |

It is seen that the molecular weight (determined by size-exclusion chromatography on cross-linked styrene/divinylbenzene column material) of the homopolymer fraction occluded amongst the grafted chains of the polystyrene-grafted polyethylene sheets and extracted from the sheets with dichloromethane increases as a function of the methanol/styrene ratio in the solution. At the same time the molecular weight distribution tends to become more narrow for high methanol/styrene ratios.

EXAMPLE 4

Experiments on the Estimation of the Molecular Weight of the Grafted Polystyrene Chains The polystyrene homopolymer extracted from the sheets was characterized by SEC. The extracted polystyrene shows typically a molecular weight distribution with two bulges. This is due to the fact that polystyrene is formed both in the sheet and in the surrounding solution during irradiation. If a sheet is washed briefly in dichloromethane before carrying out Soxhlet extraction, the amount of low molecular weight fraction is greatly reduced relative to that of the high molecular weight fraction. Molecular weight data for the high molecular weight fraction of the extracted homopolymer are given in Table 2. Typical sample sizes were from 0.01 mg to 0.2 mg of polymer. For the homopolymer from the sheets grafted to the extent of 173, 220, 231 and 450 wt %, respectively, a 60 cm column of Toyo Soda TSK GMH6 was used for SEC at ambient temperature with THF as the eluent and a flow rate of 0.5 ml/min, for the homopolymer from the sheet grafted to the extent of 443 wt %, a 50 cm column of Shodex A80-M was used for SEC at 50° C. with xylene as the solvent and a flow rate of 0.5 ml/min. This set-up was also used for SEC of the grafted polymer formed, but now operating at 90° C. and with a flow rate of approximately 0.3 ml/min. The grafted sheets are soluble in hot xylene. Molecular weight data for polystyrene-grafted polyethylene from the five grafted sheets are given in Table 4. All molecular weight data given were calculated using a calibration curve based on polystyrene standards with molecular weights from 2800 g/mol to 8,000,000 g/mol, the form of the calibration curve being fitted by a third-order polynomial. The use of a first-order (linear) calibration curve leads to similar results. It should be noted that whereas the molecular weights obtained for the styrene homopolymer are absolute, the molecular weights obtained for the graft copolymer are not absolute. In the case of the Shodex A80-M column, extrapolation of the calibration curve was necessary in order to calculate the extremely high molecular weights observed. This extrapolation may lead to underestimation of the weight average molecular weight and consequently also of the polydispersity. The ungrafted polyethylene was characterized by high-temperature SEC using 1,2,4-trichlorobenzene as the eluent. The following values were obtained: $M_w = 4 \times 10^4$ g/mol and $M_w/M_n = 5$. The latter data were obtained using a calibration curve based on polystyrene standards.

The data for the polystyrene homopolymers indicate that the molecular weight is insensitive to the total radiation dose, whereas for the polystyrene-grafted polyethylene the measured molecular weight is largely proportional to the dose. These observations indicate that the very long chain grafts are formed during the entire irradiation process and that essentially only the number of grafts is affected by the dose.

TABLE 3

Molecular weight data for the high molecular weight fraction of the polystyrene homopolymer extracted from the irradiated sheets

| Graft % | Irradiation dose (kGy) | $M_w$ # ($\times 10^{-6}$ mol/g) | $M_w/M_n$ # |
| --- | --- | --- | --- |
| 450 | 3.4 | 1.4 | 2.2 |
| 443 | 4.0 | 2.6 | 3.7 |
| 231 | 2.7 | 1.2 | 2.3 |
| 220 | 3.0 | 1.2 | 2.2 |
| 173 | 2.4 | 1.1 | 2.2 |

: $M_w$ = weight average molecular weight
: $M_w/M_n$ = weight average molecular weight divided by number average molecular weight

TABLE 4

Molecular weight data for the polystyrene-grafted polyethylene from the irradiated sheets.

| Graft % | Irradiation dose (kGy) | $M_w$ # ($\times 10^{-6}$ mol/g) | $M_w/M_n$ # | $M_{peak}$* ($\times 10^{-6}$ mol/g) |
| --- | --- | --- | --- | --- |
| 450 | 3.4 | 7.0 | 1.6 | 7.2 |
| 443 | 4.0 | 6.6 | 1.8 | 6.1 |
| 231 | 2.7 | 2.9 | 2.2 | 3.5 |
| 220 | 3.0 | 4.7 | 1.6 | 4.5 |
| 173 | 2.4 | 4.1 | 1.6 | 3.1 |

: $M_w$ = weight average molecular weight
: $M_w M_n$ = weight average molecular weight divided by number average molecular weight
*$M_{peak}$ = molecular weight at the peak point in the chromatogram

EXAMPLE 5

Reshaping of a Polystyrene-Grafted Polyethylene Sheet

A piece of 173% graft sheet (cf. Table 1) was dissolved in xylene at 100° C. and the solution poured into a teflon mold at 80° C. After slow evaporation of the xylene a very thin film was formed. Because of the extreme thinness of the film it was not possible to obtain anything but small pieces (1 to 2 mm square) of film. However, these small pieces did not disintegrate when exposed to dichloromethane. This implies that a continuous polyethylene phase is reformed.

EXAMPLE 6

Aminomethylation (Functionalization) of Polystyrene-Grafted PE Sheets

Eight equally sized rectangular strips (1.5 × 4.5 cm) of 443% polystyrene-grafted polyethylene sheet (1.30 g total) were placed in a 60 ml SPPS reaction vessel on a manual SPPS shaker and washed with 40 ml of TFA/CH$_2$Cl$_2$ (1:1 v/v) for 3×5 min. A solution of 0.35 g (1.9 mmol) N-(hydroxymethyl)phthalimide (97% purity; EGA-CHEMIE) in 40 ml of TFA/CH$_2$Cl$_2$ (1:1 v/v) was added to the washed sheets and the mixture was shaken for 10 min. 10 ml of TFMSA/TFA/CH$_2$Cl$_2$ (10:45:45 v/v/v) was added slowly over a 4–5 hour period and shaking was continued for another 3 hours. The sheets were isolated by filtration and washed sequentially with the following: TFA/CH$_2$Cl$_2$ (1:1 v/v) (120 ml), CH$_2$Cl$_2$ (240 ml), methanol (160 ml), and ethanol (160 ml). They were then shaken in 40 ml of ethanol containing 10% of hydrazine (Fluka) for 12 hours at 70° C. The sheets were filtered from the hot mixture and washed sequentially (with 20 min shaking for each wash) with the following: hot ethanol (3×40 ml), hot DMF (3×40 ml), hot ethanol (3×40 ml), hot methanol (3×40 ml), and CH$_2$Cl$_2$ (3×40 ml). Finally, the sheets were treated with 40 ml of DIEA/CH$_2$Cl$_2$ (1:9 v/v) for 2×5 min, washed with 200 ml of CH$_2$Cl$_2$, and dried at room temperature. A total of 4 spectrophotometric ninhydrin colour tests indicated 1.00 mmol NH$_2$/g sheet (0.99, 0.96, 1.02, and 1.01 mmol/g, respectively), and elemental analysis indicated 1.07 mmol N/g sheet.

The following polystyrene-grafted polyethylene sheets have also been aminomethylated:

---

331% grafted sheet: substitution = 0.21 mmol NH$_2$/g sheet.
547% grafted sheet: substitution = 0.46 mmol NH$_2$/g sheet.
129% grafted sheet: substitution = 0.50 mmol NH$_2$/g sheet.
46% grafted sheet: substitution = 0.02 mmol NH$_2$/g sheet.
285% grafted sheet: substitution = 0.6 mmol NH$_2$/g sheet.

---

EXAMPLE 7

Preparation of BocGln-4-(Oxymethyl)-Pam-Sheet 0.63 g aminomethyl-sheet (substitution-1.0 mmol/g sheet; 443% graft) was pre-washed in 30 ml DMF/CH$_2$Cl$_2$ (1:2 v/v) for 3×3 min in a 60 ml reaction vessel on a SPPS shaker. 0.98 g Boc-Gln-4-(oxymethyl)phenylacetic acid (2.5 mmol, 4 equiv.) and 0.38 g HOBt (2.5 mmol, 4 equiv.) were dissolved in 20 ml DMF/CH$_2$Cl$_2$ (1:1 v/v) and stirred in a screw-capped tube for 3 min at 0° C. 0.52 g DCC was dissolved in 10 ml CH$_2$Cl$_2$ and added to the mixture. After stirring for 25 min at 0° C., DCU was filtered off and the filtrate was added to the pre-washed aminomethyl-sheet and shaken for 2 h. The sheets were filtered, washed with CH$_2$Cl$_2$, neutralized with DIEA/CH$_2$Cl$_2$ (5:95 v/v), washed with CH$_2$Cl$_2$, and dried. The absence of positive ninhydrin tests indicated quantitative coupling, which was also confirmed after removal of the Boc group by the following treatment: 30 ml TFA/CH$_2$Cl$_2$ (1:1 v/v) for 1×2 min and 1×30 min, 30 ml CH$_2$Cl$_2$ for 6×1 min, 30 ml DIEA/CH$_2$Cl$_2$ (5:95 v/v) for 2×5 min, and 30 ml CH$_2$Cl$_2$ for 4× 1 min. 2 ninhydrin tests then indicated the extent of —NH$_2$ substitution to be 0.76 mmol NH$_2$/g sheet (0.74 and 0.77 mmol/g, respectively), which is very close to the theoretical value of 0.78 mmol NH$_2$/g sheet.

EXAMPLE 8

Peptide Synthesis: (a) Assembly of Protected Human [Asp$^{76}$]-Parathyroid Hormone Fragments 80–84, 75–84 and 70–84 on 443 wt % Polystyrene-grafted Polyethylene Sheet BocGln-OCH$_2$-Pam-sheet (0.80 g, 443% graft, 0.58 mmol Gln) was placed in a 60 ml reaction vessel on a SPPS shaker. Protected hPTH 70–84, (see FIG. 1) was assembled using the following synthetic protocol:

(1) CH$_2$Cl$_2$, 35 ml, 3×1 min;
(2) TFA/CH$_2$Cl$_2$ (1:1 v/v), 35 ml, 3×1 min;
(3) TFA/CH$_2$Cl$_2$ (1:1 v/v), 35 ml, 30 min;
(4) CH$_2$Cl$_2$, 35 ml, 6×1 min;
(5) DIEA/CH$_2$Cl$_2$ (1:19 v/v), 35 ml, 3×2 min;
(6) CH$_2$Cl$_2$, 35 ml, 6×1 min;
(7) 3 to 10 mg samples were cut off for ninhydrin analysis;
(8) protected amino acid was coupled as pre-formed symmetric anhydride (3 equiv., 0.05M) in 35 ml DMF/CH$_2$Cl$_2$ (1:4 v/v), with shaking for 2 hours;
(9) CH$_2$Cl$_2$, 35 ml, 4×2 min;
(10) 3 to 10 mg samples were cut off and neutralized by repeating (5) and (6) before ninhydrin analysis.

All couplings were single couplings. Monitoring of the synthesis by using the quantitative ninhydrin test [originally developed for peptide synthesis on beads; see e.g. Sarin et al., Anal. Biochem., 117, 147 (1981)] was successfully applied (Table 5), and with the exception (for unknown reasons) of the result for the second amino acid coupling (i.e. with formation of Boc-Ser$^{83}$(Bzl)Gln$^{84}$-OCH$_2$-Pam-sheet), indicated satisfactory values for the coupling efficiency in each coupling step.

TABLE 5

Quantitative ninhydrin monitoring[a] of the solid-phase synthesis of protected human parathyroid hormone fragment (70–84) on 443 wt % polystyrene-grafted polyethylene

| Residue coupled | Coupling[b] Remaining free amino groups (μmol/g) | Deprotection | | |
|---|---|---|---|---|
| | | Estimated[c] % completion | Measured substitution (mmol/g) | Theoretical substitution (mmol/g) |
| 84 BocGlnX[d] | 0.0 | 100 | 0.76 ± 0.02 | 0.78 |
| 83 BocSer(Bzl) | 38.0 | 94.0 | 0.35 ± 0.04 | 0.69 |
| 82 BocLys(2Cl-Z) | 1.6 | 99.7 | 0.54 ± 0.03 | 0.57 |
| 81 BocAla | 0.6 | 99.9 | 0.52 ± 0.03 | 0.55 |
| 80 BocLys(2Cl-Z) | 1.2 | 99.7 | 0.53 ± 0.02 | 0.47 |
| 79 BocThr(Bzl) | 0.0 | 100 | 0.44 ± 0.03 | 0.43 |
| 78 BocLeu | 0.4 | 99.9 | 0.39 ± 0.01 | 0.41 |
| 77 BocVal | 0.0 | 100 | 0.39 ± 0.03 | 0.40 |
| 76 BocAsp(OBzl) | 0.0 | 100 | 0.35 ± 0.01 | 0.37 |
| 75 BocVal | 0.2 | 99.9 | 0.31 ± 0.02 | 0.35 |
| 74 BocAsp(OBzl) | 0.7 | 99.8 | 0.31 ± 0.02 | 0.33 |
| 73 BocAla | 0.0 | 100 | 0.29 ± 0.01 | 0.33 |
| 72 BocLys(2Cl-Z) | 1.1 | 99.6 | 0.30 ± 0.02 | 0.30 |

TABLE 5-continued

Quantitative ninhydrin monitoring[a] of the solid-phase synthesis of protected human parathyroid hormone fragment (70–84) on 443 wt % polystyrene-grafted polyethylene

| Residue coupled | Coupling[b] Remaining free amino groups ($\mu$mol/g) | Deprotection Estimated[c] % completion | Measured substitution (mmol/g) | Theoretical substitution (mmol/g) |
|---|---|---|---|---|
| 71 BocAsp(OBzl) | 1.3 | 99.5 | 0.28 ± 0.02 | 0.28 |
| 70 BocAla | 0.0 | 100 | 0.23 ± 0.01 | 0.27 |

[a]Average values based on 2-4 ninhydrin analyses after coupling and deprotection in each cycle expressed as mmol/g of peptide-sheet.
[b]No residues were recoupled, but coupling of Boc—Ser(Bzl) was followed by complete acetylation of remaining free amino groups using N-acetylimidazole in methylene chloride.
[c]These estimated values are calculated relative to the theoretical substitution after coupling of the Boc-protected residue, and do not include correction for incomplete coupling of the preceding residue.

(b) Cleavage, purification and identification of synthetic hPTH-(80-84)

90 mg of H-Lys(ClZ)AlaLys(ClZ)Ser(Bzl)Gl-nOCH$_2$-Pam-sheet was treated with 5 ml of anhydrous HF/anisole (9:1 v/v) for 1 h at 0° C. to simultaneously deprotect the side-chain protecting groups and cleave the peptide from the sheet. Extractions with ether, to remove organic components such as anisole and alkylated anisoles, were followed by extraction into 10% aqueous acetic acid. Lyophilization gave 24.0 mg of crude product of high purity [see HPLC chromatogram in FIG. 2(A)].

The crude product was purified in two steps on a perparative C$_{18}$ column (300×19 mm). Buffers including TFA were evaporated off under reduced pressure and the product was redissolved in water; the solution was filtered and lyophilized to give 17.8 mg of H-LysAlaLysSerGln-OH, as confirmed by amino acid analysis (Table 6) and FABMS molecular weight measurements (Table 7).

The overall synthetic yield was approx. 84%, and the yield of pure peptide was approx. 69% based on the quantitative amino acid analysis.

(c) Cleavage, purification and identification of synthetic hPTH-(75-84)

93 mg of H-ValAsp(OBzl)ValLeuThr(Bzl)Lys(ClZ)AlaLys(ClZ)Ser(Bzl)Gln-OCH$_2$-Pam-sheet was treated in the same manner as for hPTH-(80-84), giving 36.6 mg of crude product [see HPLC chromatogram in FIG. 2(B)], and finally 27.2 mg of purified peptide, identified by amino acid analysis (Table 6) and molecular weight measurements (Table 7). The overall synthetic yield was approx. 85%, and the yield of pure peptide was approx. 69%, based on the quantitative amino acid analysis.

(d) Cleavage, purification and identification of synthetic hPTH-(70-84)

The hPTH-(70-84) fragment was released from 96 mg of peptide-sheet in the same way as in (b) and (c), above [see HPLC chromatogram in FIG. 2(C)]. The overall synthetic yield was approx. 83% and the yield of pure peptide was 26 mg (approx. 63%). The pure peptide was identified by amino acid analysis (Table 6) and molecular weight measurements (Table 7).

TABLE 6

Amino acid composition of purified synthetic hPTH compounds

| Amino acid | Molar ratio[a] | | |
|---|---|---|---|
| | hPTH-(70-84) | hPTH-(75-84) | hPTH-(80-84) |
| Asp | 2.94 (3) | 1.01 (1) | — |
| Thr[b] | 0.99 (1) | 0.95 (1) | — |
| Ser[b] | 1.05 (1) | 0.81 (1) | 0.94 (1) |
| Glu | 1.31 (1) | 1.03 (1) | 1.07 (1) |
| Ala | 3.00 (3) | 1.00 (1) | 1.00 (1) |
| Val | 2.00 (2) | 2.00 (2) | — |
| Leu | 1.03 (1) | 1.00 (1) | — |
| Lys | 3.08 (3) | 1.98 (2) | 1.89 (2) |

Hydrolyses were performed in sealed, evacuated tubes with 5.7 M HCl containing 0.05% phenol, 110° C., 20 h. Analysis by HPLC using fluorescence detection (338/450 nm) following treatment (post-column) with an o-phthaldialdehyde derivatizing reagent.
[a]Values in parentheses are theoretical.
[b]Thr and Ser values were not corrected for loss during hydrolysis.

TABLE 7

Molecular weights of hPTH compounds

| Peptide | Molecular weight | |
|---|---|---|
| | measured | calculated |
| hPTH-(80-84) | 560.3 | 560.3 |
| hPTH-(75-84) | 1088 | 1088 |
| hPTH-(70-84) | 1588 | 1588 |

Determined by quadrupole mass spectrometry. The calculated m/z values are for C=12.000 u and H=1.008 u.

EXAMPLE 9

Rapid Parallel Synthesis of Multiple Peptide Analogs (a) Labeling of Sheets

Aminomethylated 285 wt % polystyrene-grafted polyethylene sheet (0.6 mmol NH$_2$/g sheet) was cut into thirteen discrete pieces (each piece: 1.5×3 cm, ca. 50 $\mu$m thickness, ca. 40 mg) and labeled individually by means of graphite-based ink. A piece of polyethylene film was placed on top of each labeled surface and melted into the grafted sheet by using an electrically heated sealing apparatus. Finally, the sheets were shaken in 50% TFA/CH$_2$Cl$_2$ for 20 min. to check that all labels were adequately sealed in.

(b) Simultaneous Synthesis of Melittin-(7-21) and Twelve Analogs on Labeled Sheets Protected melittin-(7-21), i.e.

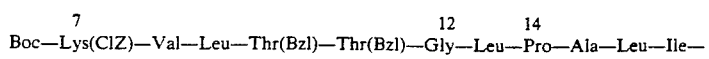

Boc—Lys(ClZ)—Val—Leu—Thr(Bzl)—Thr(Bzl)—Gly—Leu—Pro—Ala—Leu—Ile—

21
Ser(Bzl)—Trp(CHO)—Ile—Lys(ClZ)—Pam—sheet, and twelve analogs derived by substitutions in positions 12 and 14 (sequences of the free peptides are listed in FIG. 3) were each assembled stepwise on a labeled sheet. The common steps of deprotection, neutralization, washing and coupling of identical amino acids were performed simultaneously in a single reaction vessel, while the coupling of different amino acids was carried out in separate vessels.

A standard solid-phase procedure was employed, using double DCC coupling (3.5 equiv., 0.05M, in 30% DMF/CH$_2$Cl$_2$) of all residues except for Boc-Gln and Boc-Asn, which were double coupled as HOBt esters in 30% DMF/CH$_2$Cl$_2$, and Boc-Leu$^{13}$ to Gln$^{14}$, which was double coupled as a symmetric anhydride in 20% DMF/CH$_2$Cl$_2$.

Figure 4:
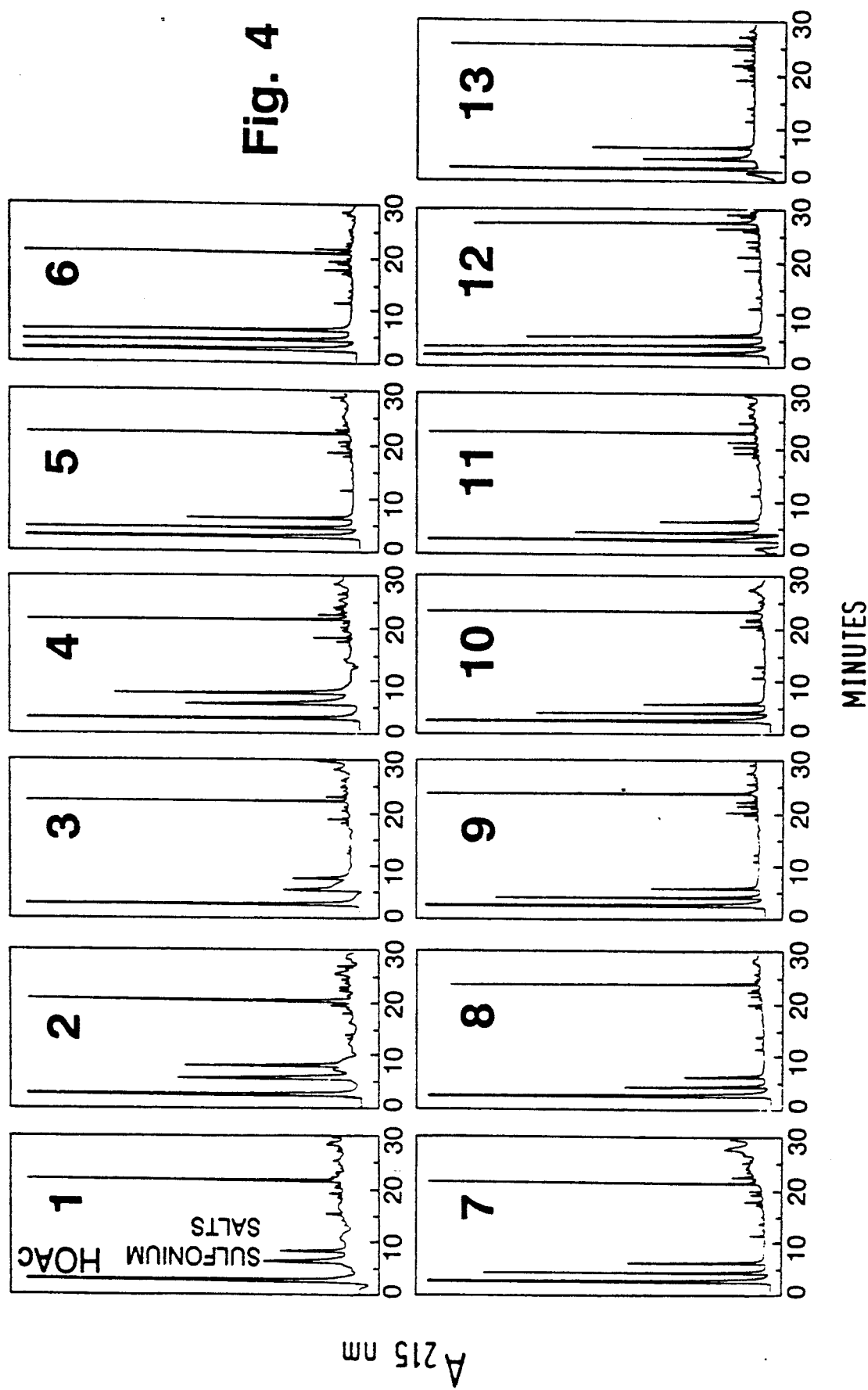

Following removal of the N-terminal Boc group, deprotection and release of the peptides from the sheets were accomplished by the low/high HF method (Tam et al., *J. Am. Chem. Soc.*, 105, 6442 (1983)). The free 15-residue peptides were obtained in overall synthetic yields of ca. 70%. FIG. 4 shows HPLC chromatograms of the thirteen unpurified peptides. All peptides were purified in 1-2 steps on a semi-preparative C$_{18}$ column. As an example, 3.2 mg of pure melittin-(7-21) was obtained from 1 cm$^2$ (23.2 mg) of fully protected peptide-sheet. The identity of the peptides was verified by amino acid analysis (Table 8) and molecular weight measurements (Table 9).

TABLE 9-continued

| Molecular weights of melittin-(7-21) analogs$^a$ | | | |
|---|---|---|---|
| | Molecular weight | | |
| Peptide | measured | calculated | Δ$^b$ |
| 13 | 1727.3 | 1727.2 | +0.1 |

$^a$Determined by $^{252}$Cf fission fragment time of flight mass spectrometry from the mean of the most abundant isotopes.
$^b$Δ = measured − calculated.

We claim:
1. A method for the synthesis of a peptide or protein, the method comprising the steps of:
   A) providing a polymer substrate grafted with polystyrene chains, said polystyrene chains being selected from the group consisting of unsubstituted polystyrene chains and polystyrene chains bearing substituents which are not reactive under the conditions prevailing in the synthesis, the estimated peak molecular weight of the polystyrene chains grafted to the polymer, not including substituents, being at least 200,000, the polystyrene moiety of the polystyrene-grafted polymer substrate being functionalized with a chemical functionality facilitating the formation of an anchoring linkage between the polystyrene moiety and an at least N-protected amino acid selected from the group consisting of i) N-protected and, when applicable, side chain protected amino acids and ii) N-protected

TABLE 8

| Amino acid composition of purified melittin-(7-21) and its analogs | | | | | | | | | | | | | |
|---|---|---|---|---|---|---|---|---|---|---|---|---|---|
| | Molar ratio$^a$ | | | | | | | | | | | | |
| Amino acid | pept. 1 | pept. 2 | pept. 3 | pept. 4 | pept. 5 | pept. 6 | pept. 7 | pept. 8 | pept. 9 | pept. 10$^d$ | pept. 11 | pept. 12 | pept. 13 |
| Lys | 1.95 (2) | 1.69 (2) | 1.77 (2) | 2.83 (3) | 1.47 (2) | 1.87 (2) | 1.71 (2) | 1.83 (2) | 1.93 (3) | (2) | 1.75 (2) | 1.66 (2) | 2.62 (3) |
| Val | 0.65 (1) | 0.82 (1) | 0.87 (1) | 0.78 (1) | 0.87 (1) | 0.88 (1) | 0.81 (1) | 0.88 (1) | 0.87 (1) | (1) | 1.75 (2) | 0.81 (1) | 0.89 (1) |
| Leu | 2.97 (3) | 2.85 (3) | 2.94 (3) | 2.67 (3) | 2.86 (3) | 2.92 (3) | 2.93 (3) | 3.90 (4) | 3.06 (3) | (3) | 2.73 (3) | 3.70 (4) | 3.71 (4) |
| Thr$^b$ | 1.87 (2) | 1.89 (2) | 1.93 (2) | 1.70 (2) | 1.84 (2) | 1.87 (2) | 1.90 (2) | 1.88 (2) | 2.06 (2) | (2) | 1.92 (2) | 1.62 (2) | 1.93 (2) |
| Gly | 1.08 (1) | 1.03 (1) | 2.04 (2) | 1.07 (1) | 1.12 (1) | 1.09 (1) | 1.08 (1) | 1.05 (1) | 1.26 (1) | (1) | 1.05 (1) | — | — |
| Pro | 0.98 (1) | 0.98 (1) | — | — | — | — | — | — | — | | | | |
| Ala | 1.00 (1) | 1.00 (1) | 1.00 (1) | 1.00 (1) | 1.00 (1) | 1.00 (1) | 1.00 (1) | 1.00 (1) | 1.00 (1) | (1) | 1.00 (1) | 1.00 (1) | 1.00 (1) |
| Ile | 1.93 (2) | 1.75 (2) | 1.81 (2) | 1.75 (2) | 1.77 (2) | 1.82 (2) | 1.80 (2) | 1.83 (2) | 1.95 (2) | (2) | 1.73 (2) | 1.73 (2) | 1.80 (2) |
| Ser$^b$ | 0.90 (1) | 0.96 (1) | 0.97 (1) | 1.00 (1) | 0.98 (1) | 0.95 (1) | 1.88 (2) | 0.95 (1) | 1.01 (1) | (1) | 0.97 (1) | 1.00 (1) | 0.95 (1) |
| Trp$^c$ | | | | | | | | | | | | | |
| Asp | — | — | — | — | (1) | 1.04 (1) | — | — | — | | | | |
| Phe | | | | | | | | — | 0.91 (1) | (1) | | | |
| Glu | | | | | | | | | | | — | 1.12 (1) | — |

The peptides were hydrolyzed in 5.7 M HCl at 110° C. for 18 h in sealed non-evacuated tubes, except peptide 1 which was hydrolyzed for 24 h in an evacuated tube. After filtration, hydrolysates were analyzed on a Beckman 6300 amino acid analyzer.
$^a$Values in parentheses are theoretical.
$^b$Thr and Ser values were not corrected for loss during hydrolysis.
$^c$Tryptophan was not determined.
$^d$Peptide analog number 10 was not analyzed.

TABLE 9

| Molecular weights of melittin-(7-21) analogs$^a$ | | | |
|---|---|---|---|
| | Molecular weight | | |
| Peptide | measured | calculated | Δ$^b$ |
| 1 | 1640.5 | 1640.0 | +0.5 |
| 2 | 1640.1 | 1640.0 | +0.1 |
| 3 | 1600.0 | 1599.9 | +0.1 |
| 4 | 1671.2 | 1671.1 | +0.1 |
| 5 | 1658.0 | 1658.0 | 0.0 |
| 6 | 1657.0 | 1657.0 | 0.0 |
| 7 | 1630.2 | 1630.0 | +0.2 |
| 8 | 1656.1 | 1656.0 | +0.1 |
| 9 | 1690.0 | 1690.1 | −0.1 |
| 10 | 1690.3 | 1690.1 | +0.2 |
| 11 | 1642.2 | 1642.0 | +0.2 |
| 12 | 1727.4 | 1727.1 | +0.3 | and carboxyl terminal derivatized and, when applicable, side chain protected amino acids,
   B) covalently coupling a said at least N-protected amino acid to the functionalized polystyrene moiety, said functionality and said at least N-protected amino acid being adapted to each other such that the anchoring linkage formed can subsequently be cleaved substantially without degradation of the peptide or protein chain which is to be synthesized,
   C) removing the N-protecting group from an N-protected group of the coupled and N-protected amino acid, the group which is N-protected being selected from the group consisting of amino and substituted amino, such that reaction of the now unprotected said group of the coupled amino acid with a carboxyl terminal group of a further said at least N-protected amino acid is facilitated, said carboxyl terminal group being selected from the group consisting of carboxyl and activated carboxyl, D) reacting said now unprotected group of the last-coupled amino acid with a said carboxyl terminal group of a further said at least N-protected amino acid so as to form a peptide bond between the two amino acid moieties, E) when applicable removing the N-protecting group from an N-protected group of the last-coupled N-protected amino acid, the group which is N-protected being selected from the group consisting of amino and substituted amino, such that reaction of the now unprotected said group of said last-coupled amino acid with a said carboxyl terminal group of a further said at least N-protected amino acid is facilitated, F) when step E) has been performed, repeating steps D) and E) a desired number of times, G) when applicable removing protecting groups remaining on the amino acid moieties of the synthesized peptide or protein chain, H) when applicable cleaving the linkage anchoring the synthesized peptide or protein chain to the functionalized polystyrene moiety, and I) when applicable removing any further undesired group from the synthesized peptide or protein chain.

2. A method as claimed in claim 1, wherein the estimated peak molecular weight of the polystyrene chains grafted to the polymer, not including substituents, is in the range of 300,000–1,600,000.

3. A method as claimed in claim 1, wherein said polystyrene-grafted polymer substrate has been prepared from a polymer substrate in the form of a sheet or film of thickness in the range of 25 to 100 μm, and the degree of polystyrene chain grafting of the polymer substrate is in the range of 5–800% by weight.

4. A method as claimed in claim 1, wherein said polystyrene-grafted polymer substrate has been formed by a substantially radical-initiated reaction between the polymer substrate and a styrene monomer present in a solution of said monomer in an organic solvent.

5. A method as claimed in claim 4, wherein the organic solvent which has been used to dissolve the styrene monomer is an alcohol.

6. A method as claimed in claim 4, wherein the volume percentage (% v/v) of styrene monomer in the solution which has been used is such that $1 \leq \%\ v/v \leq 95$.

7. A method as claimed in claim 1, wherein said polystyrene-grafted polymer substrate is in the form of a sheet or film.

8. A method as claimed in claim 7, wherein the sheet or film has a thickness of from 10 to 10,000 μm.

9. A method as claimed in claim 1, wherein the chemical functionality facilitating the formation of an anchoring linkage between an at least N-protected amino acid and the functionalized polystyrene moiety is selected from the group consisting of:

chloro-, bromo- and iodo-substituted alkyl and derivatives thereof;

amino- and aryl-substituted alkyl and derivatives thereof;

amino- and alkylaryl-substituted alkyl and derivatives thereof;

hydroxy-substituted alkyl and derivatives thereof; and amino-substituted alkyl and derivatives thereof, said derivatives being functionalities with a spacer group such that a synthesized peptide or protein chain will be cleavable from the polystyrene moiety substantially without degradation of said chain.

10. A method as claimed in claim 1, wherein said polystyrene-grafted polymer substrate has been prepared from a polymer substrate in the form of a sheet or film of thickness in the range of 25 to 100 μm, and the degree of polystyrene chain grafting of the polymer substrate is in the range of 100–600% by weight.

11. A method as claimed in claim 1, wherein said polystyrene-grafted polymer substrate has been prepared from a polymer substrate in the form of a sheet or film of thickness in the range of 25 to 100 μm, and the degree of polystyrene chain grafting of the polymer substrate is in the range of 200–400% by weight.

12. A method as claimed in claim 4, wherein the organic solvent which has been used to dissolve the styrene monomer is a $C_{1-4}$ aliphatic alcohol.

13. A method as claimed in claim 4, wherein the organic solvent which has been used to dissolve the styrene monomer is methanol.

14. A method as claimed in claim 4, wherein the volume percentage (% v/v) of styrene monomer in the solution which has been used is such that $25 \leq \%\ v/v \leq 35$.

15. A method as claimed in claim 7, wherein the sheet or film has a thickness of from 25 to 200 μm.

16. A method as claimed in claim 1, wherein the chemical functionality facilitating the formation of an anchoring linkage between an at least N-protected amino acid and the functionalized polystyrene moiety is selected from the group consisting of:

chloromethyl and derivatives thereof;

α-aminobenzyl and derivatives thereof;

α-amino-2-, α-amino-3- and α-amino-4-methylbenzyl and derivatives thereof;

hydroxymethyl and derivatives thereof; and aminomethyl and derivatives thereof, said derivatives being functionalities with a spacer group such that a synthesized peptide or protein chain will cleavable from the polystyrene moiety substantially without degradation of said chain.

17. A method as claimed in claim 1, wherein the polymer is a polyolefin.

18. A method as claimed in claim 1, wherein the polymer is polyethylene.

19. A method for the synthesis of peptides or proteins, which method when two or more peptides or proteins are to be synthesized, permits the parallel and substantially simultaneous synthesis of the desired number of peptides or proteins, the method comprising:

A) providing a plurality of substantially identical polymer substrates grafted with polystyrene chains, said polystyrene chains being selected from the group consisting of unsubstituted polystyrene chains and polystyrene chains bearing substituents which are not reactive under the conditions prevailing in the synthesis, the estimated peak molecular weight of the polystyrene chains grafted to the polymer, not including substituents, being at least 200,000, the polystyrene moiety of each polystyrene-grafted polymer substrate being functionalized with a chemical functionality facilitating the formation of an anchoring linkage between the polystyrene moiety and an at least N-protected amino acid selected from the group consisting of i) N-protected and, when applicable, side chain protected amino acids and ii) N-protected and carboxyl terminal derivatized and, when applicable, side chain protected amino acids, B) when applicable physically segregating the members of said plurality of polystyrene-grafted polymer substrates into at least two sets each comprising at least one member of said plurality, covalently coupling a said at least N-protected amino acid to the functionalized polystyrene moiety of the members of said plurality or sets, the at least N-protected amino acid employed being identical for all the members of said plurality or of one said set and, when applicable, further being in accordance with one of the following:
 (i) identical for all sets,
 (ii) different for each set,
 (iii) when the number of said sets is greater than two, identical for at least two of the sets,
 said functionality and said at least N-protected amino acid being adapted to each other such that the anchoring linkage formed can subsequently be cleaved substantially without degradation of the peptide or protein chain which is to be synthesized, C) treating each member of said plurality or sets so as to remove the N-protecting group from an N-protected group of the coupled and N-protected amino acid, the group which is N-protected being selected from the group consisting of amino and substituted amino, such that reaction of the now unprotected said group of the coupled amino acid with a carboxyl terminal group of a further said at least N-protected amino acid is facilitated, said carboxyl terminal group being selected from the group consisting of carboxyl and activated carboxyl, D) reacting said now unprotected group of the amino acid last coupled to the functionalized polystyrene moiety of the members of said plurality of sets with a said carboxyl terminal group of a further said at least N-protected amino acid so as to form a peptide bond between the two amino acid moieties, the further said at least N-protected amino acid being identical for all the members of said plurality or of one said set, and, when applicable, further being in accordance with one of (i), (ii) and (iii) above, E) when applicable treating each member of said plurality or sets so as to remove the N-protecting group from an N-protected group of the last-coupled N-protected amino acid, the group which is N-protected being selected from the group consisting of amino and substituted amino, such that reaction of the now unprotected said group of said last-coupled amino acid with a said carboxyl terminal group of a further said at least N-protected amino acid is facilitated, F) when step E) has been performed, repeating steps D) and E) a desired number of times, G) when applicable treating each member of said plurality or sets so as to remove protecting groups remaining on the amino acid moieties of the synthesized peptide or protein chain, H) when applicable treating each member of said plurality or sets so as to cleave the linkage anchoring the synthesized peptide or protein chain to the functionalized polystyrene moiety, and I) when applicable removing any further undesired group from a synthesized peptide or protein chain.

20. A method as claimed in claim 19, wherein the estimated peak molecular weight of the polystyrene chains grafted to the polymer, not including substituents, is in the range of 300,000–1,600,000.

21. A method as claimed in claim 19, wherein said polystyrene-grafted polymer substrates have been prepared from a polymer substrate in the form of a sheet or film of thickness in the range of 25 to 100 $\mu$m, and the degree of polystyrene chain grafting of the polymer substrate is in the range of 5–800% by weight.

22. A method as claimed in claim 19, wherein said polystyrene-grafted polymer substrates have been prepared from a polymer substrate in the form of a sheet or film of thickness in the range of 25 to 100 $\mu$m, and the degree of polystyrene chain grafting of the polymer substrate is in the range of 100–600% by weight.

23. A method as claimed in claim 19, wherein said polystyrene-grafted polymer substrates have been prepared from a polymer substrate in the form of a sheet or film of thickness in the range of 25 to 100 $\mu$m, and the degree of polystyrene chain grafting of the polymer substrate is in the range of 200–400% by weight.

24. A method as claimed in claim 19, wherein said polystyrene-grafted polymer substrates have been formed by a substantially radical-initiated reaction between the polymer substrate and a styrene monomer present in a solution of said monomer in an organic solvent.

25. A method as claimed in claim 24, wherein the organic solvent which has been used to dissolve the styrene monomer is an alcohol.

26. A method as claimed in claim 24, wherein the organic solvent which has been used to dissolve the styrene monomer is a $C_{1-4}$ aliphatic alcohol.

27. A method as claimed in claim 24, wherein the organic solvent which has been used to dissolve the styrene monomer is methanol.

28. A method as claimed in claim 24, wherein the volume percentage (% v/v) of the styrene monomer in the solution which has been used is such that $1 \leq \% \text{ v/v} \leq 95$.

29. A method as claimed in claim 24, wherein the volume percentage (% v/v) of styrene monomer in the solution which has been used is such that $25 \leq \% \text{ v/v} \leq 35$.

30. A method as claimed in claim 19, wherein said polystyrene-grafted polymer substrates are in the form of a sheet or film.

31. A method as claimed in claim 30, wherein the sheet or film has a thickness of from 10 to 10,000 $\mu$m.

32. A method as claimed in claim 30, wherein the sheet or film has a thickness of from 25 to 200 $\mu$m.

33. A method as claimed in claim 19, wherein the chemical functionality facilitating the formation of an anchoring linkage between an at least N-protected amino acid and the functionalized polystyrene moiety is selected from the group consisting of:
 chloro-, bromo- and iodo-substituted alkyl and derivatives thereof;
 amino- and aryl-substituted alkyl and derivatives thereof;
 amino- and alkylaryl-substituted alkyl and derivatives thereof;

hydroxy-substituted alkyl and derivatives thereof; and amino-substituted alkyl and derivatives thereof, said derivatives being functionalities with a spacer group such that a synthesized peptide or protein chain will be cleavable from the polystyrene moiety substantially without degradation of said chain.

34. A method as claimed in claim 19, wherein the chemical functionality facilitating the formation of an anchoring linkage between an at least N-protected amino acid and the functionalized polystyrene moiety is selected from the group consisting of:

chloromethyl and derivatives thereof;

α-aminobenzyl and derivatives thereof;

α-amino-2-,α-amino-3- and α-amino-4-methylbenzyl and derivatives thereof;

hydroxymethyl and derivatives thereof; and aminomethyl and derivatives thereof, said derivatives being functionalities with a spacer group such that a synthesized peptide or protein chain will be cleavable from the polystyrene moiety substantially without degradation of said chain.

35. A method as claimed in claim 19, wherein the polymer is a polyolefin.

36. A method as claimed in claim 19, wherein the polymer is polyethylene.

* * * * *